United States Patent
Therin

(10) Patent No.: US 6,685,629 B2
(45) Date of Patent: Feb. 3, 2004

(54) SUBURETHRAL SUPPORT ASSEMBLY IN TREATMENT OF FEMALE URINARY STRESS INCONTINENCE

(75) Inventor: Michel Therin, Lyons (FR)

(73) Assignee: Sofradim Production, Trevoux (FR)

( * ) Notice: Subject to any disclaimer, the term of this patent is extended or adjusted under 35 U.S.C. 154(b) by 0 days.

(21) Appl. No.: 10/151,982

(22) Filed: May 22, 2002

(65) Prior Publication Data

US 2003/0004395 A1 Jan. 2, 2003

Related U.S. Application Data

(63) Continuation-in-part of application No. PCT/FR01/03027, filed on Oct. 1, 2001.

(30) Foreign Application Priority Data

Oct. 5, 2000 (FR) .............................................. 00 12750

(51) Int. Cl.$^7$ ................................................. A61F 2/00
(52) U.S. Cl. ......................................................... 600/37
(58) Field of Search .............................. 600/29, 30, 37; 128/DIG. 25, 897, 898; 606/118–119, 138, 139, 140, 141, 145, 222, 223–228

(56) References Cited

U.S. PATENT DOCUMENTS

| | | | | | |
|---|---|---|---|---|---|
| 5,899,909 A | * | 5/1999 | Claren et al. | ................ | 606/119 |
| 6,273,853 B1 | * | 8/2001 | Cartier et al. | ................ | 600/229 |
| 6,406,423 B1 | * | 6/2002 | Scetbon | ........................ | 600/30 |
| 6,478,727 B2 | * | 11/2002 | Scetbon | ........................ | 600/30 |
| 2002/0091373 A1 | * | 7/2002 | Berger | ........................... | 606/1 |

* cited by examiner

Primary Examiner—Samuel G. Gilbert
(74) Attorney, Agent, or Firm—Oliff & Berridge, PLC

(57) ABSTRACT

An assembly includes a suburethral supporting strip and a needle or similar sharp part designed to pass through the skin, and a composite band including at least a flat protective sheath, the suburethral supporting strip being disposed for example freely inside this sheath; the flat sheath including, in its lengthwise direction, two parts disposed on either side of a central separation area and at each of its two ends the composite band has a single part of a lockable and unlockable connecting device, while the needle has at least one other part of a connecting device, the connecting device of the composite band and each connecting device of the needle enabling the needle to be connected releasably to at least one of the ends of the composite band.

35 Claims, 15 Drawing Sheets

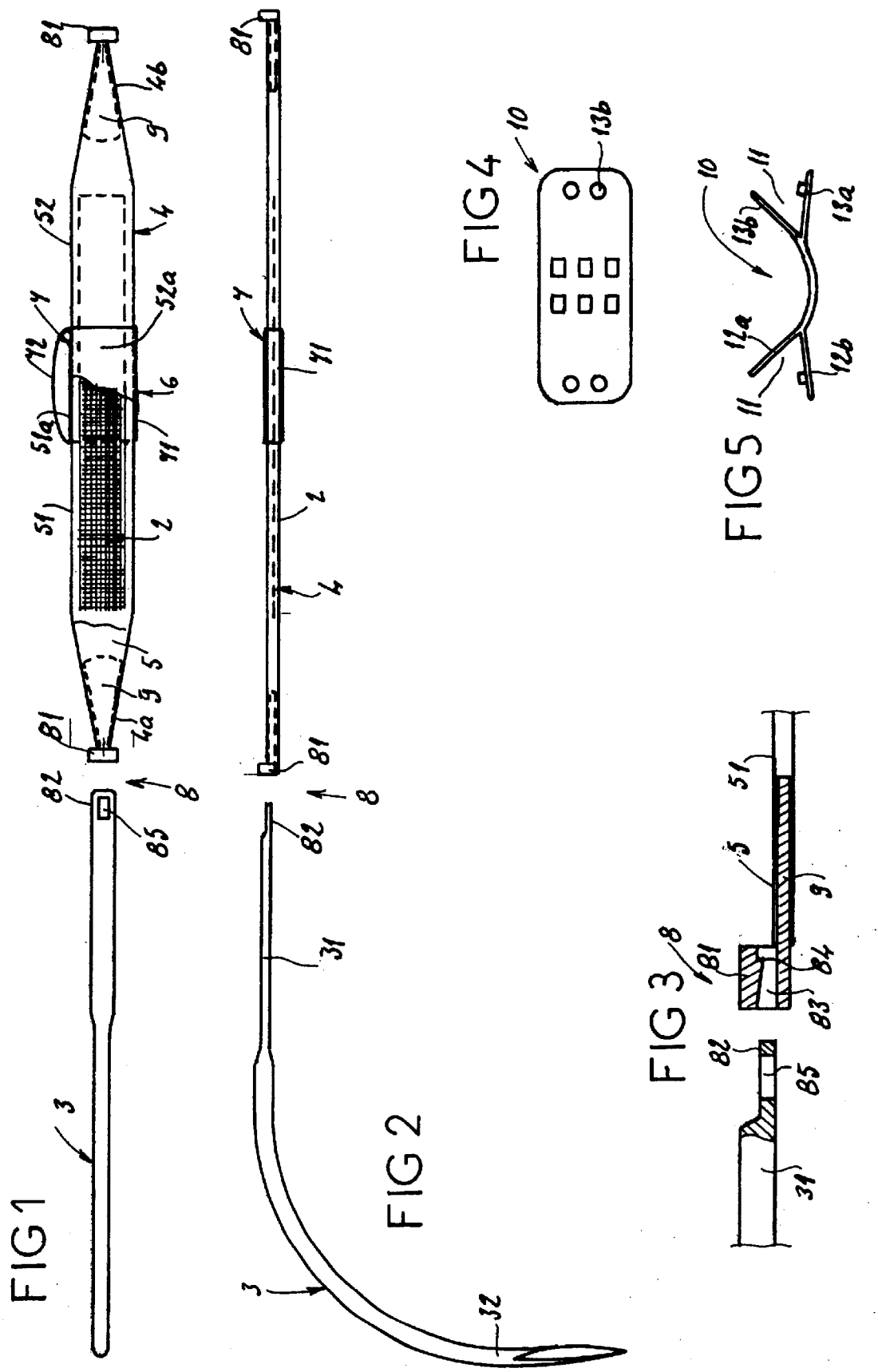

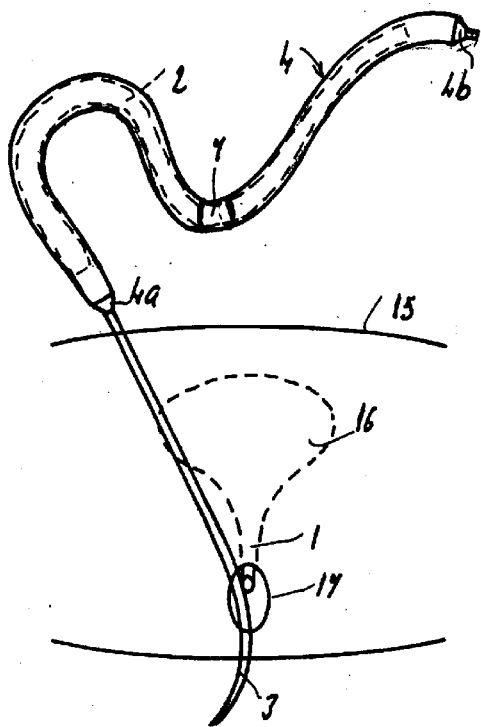
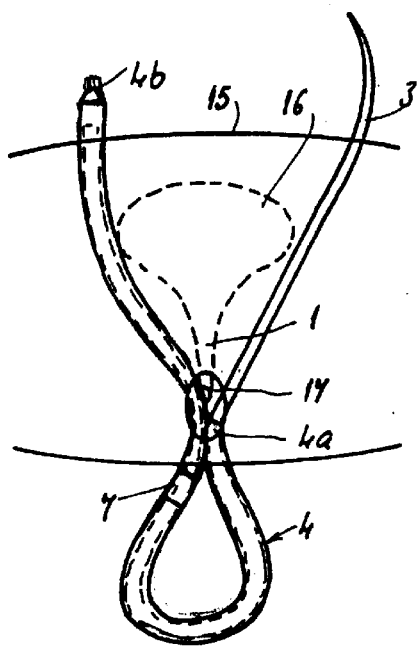
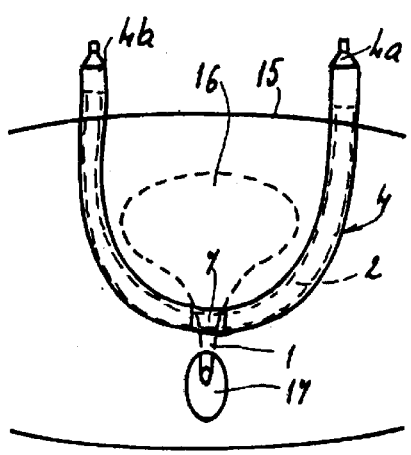
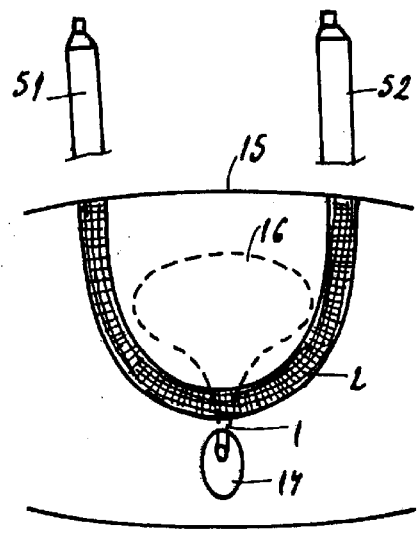

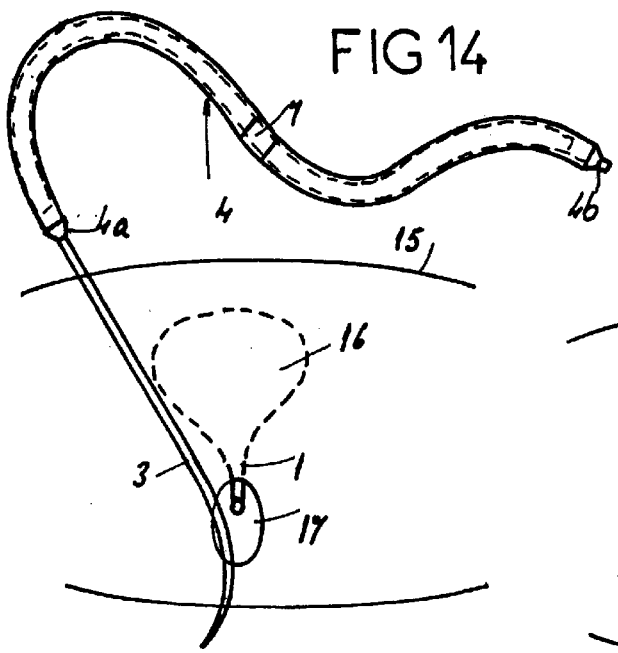
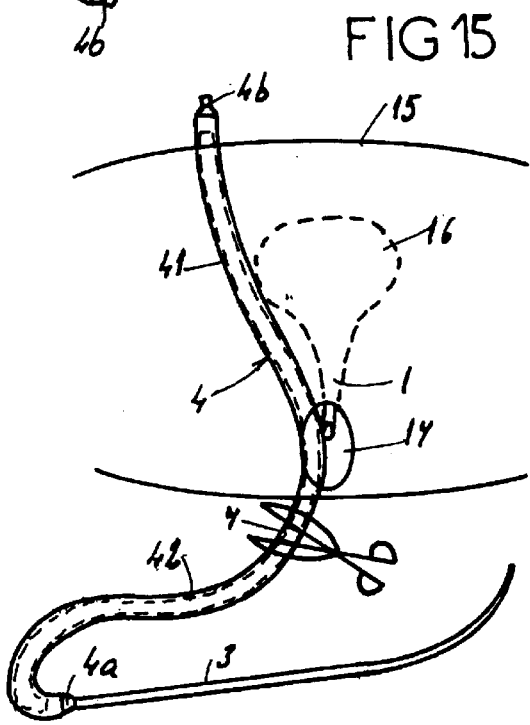
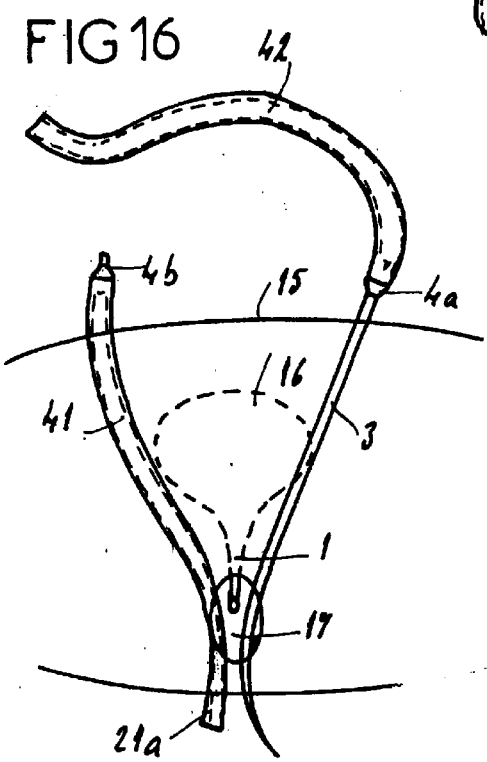
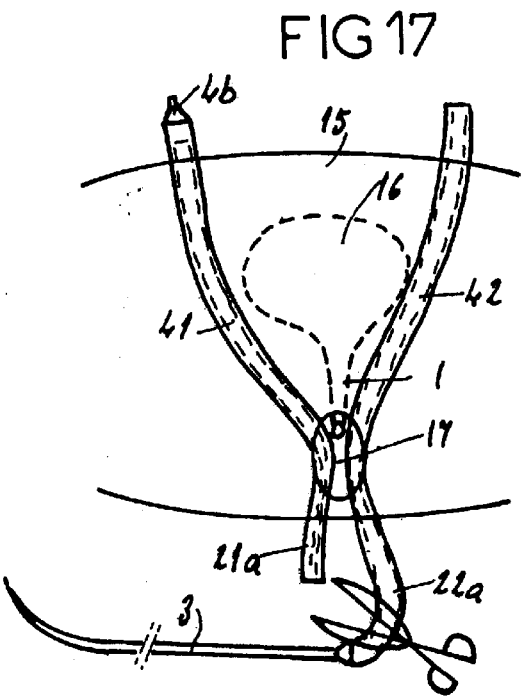

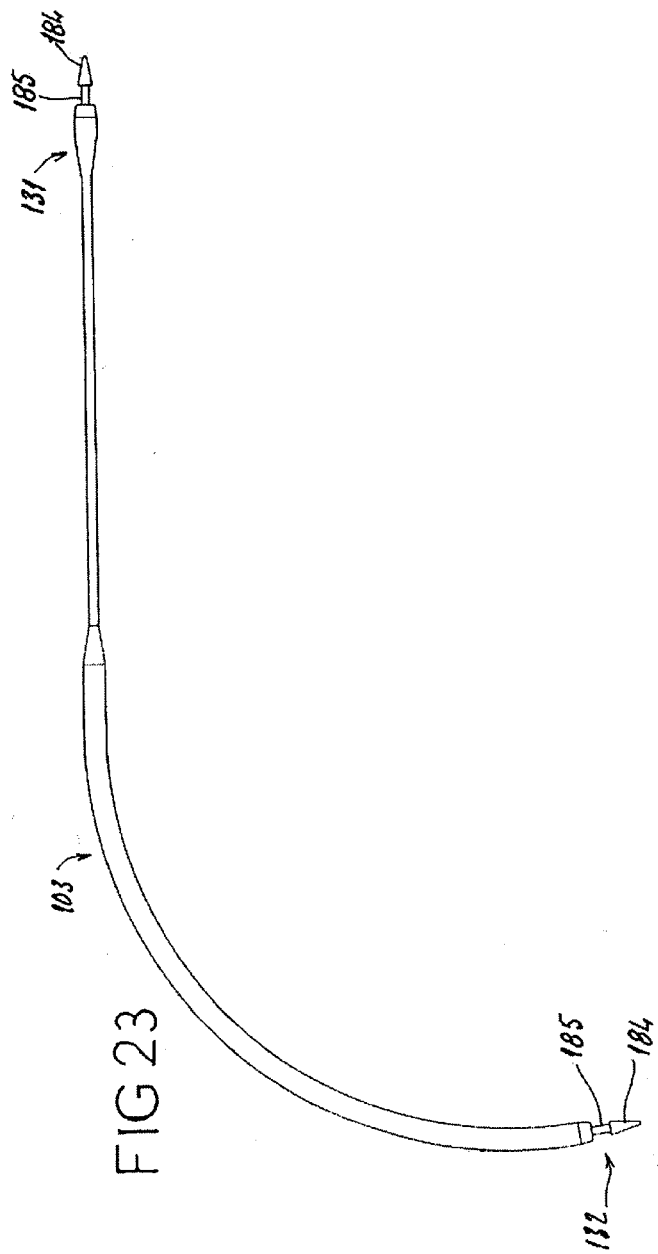

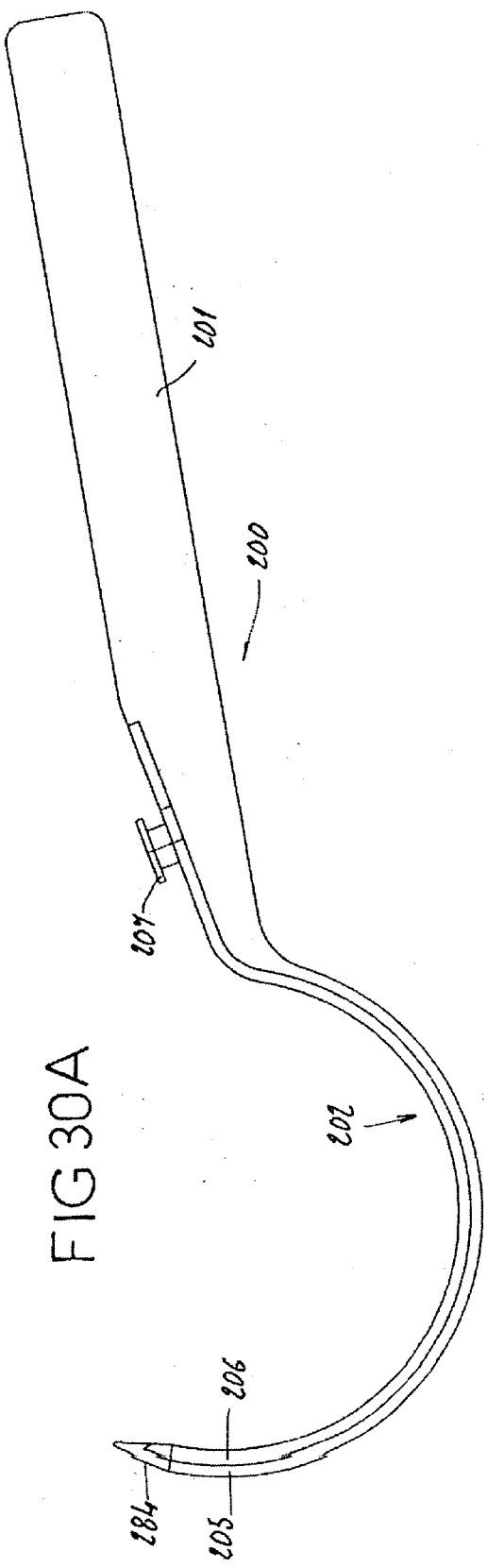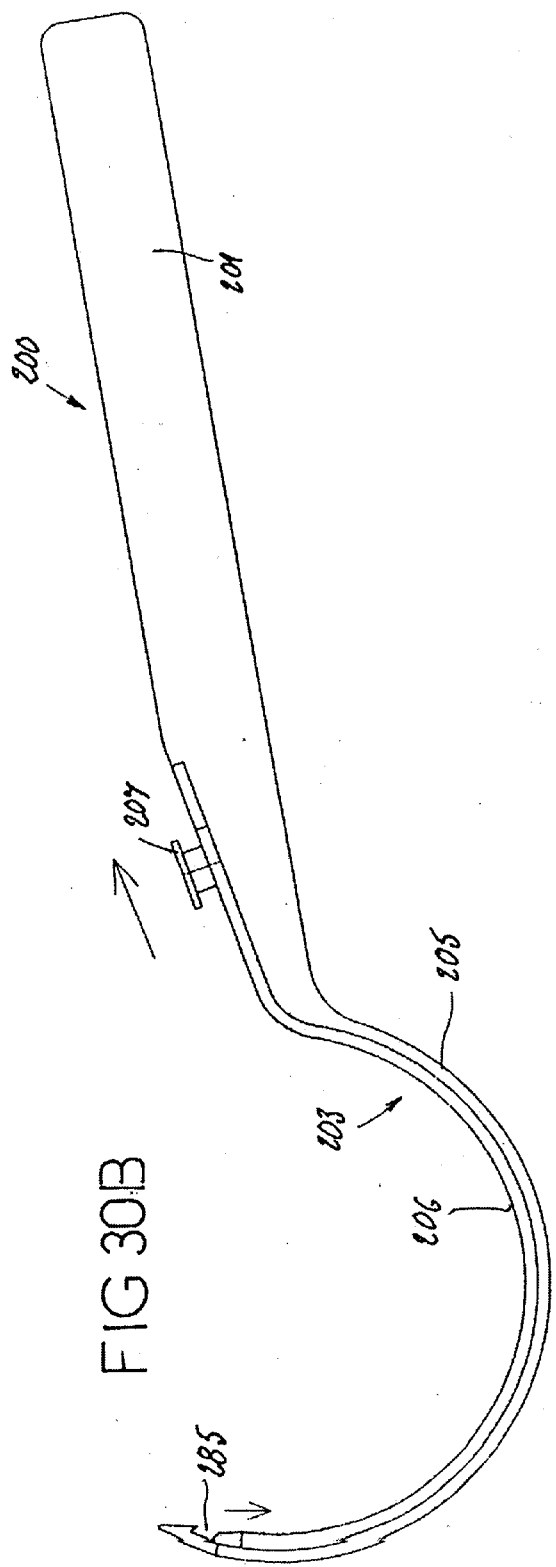

US 6,685,629 B2

SUBURETHRAL SUPPORT ASSEMBLY IN TREATMENT OF FEMALE URINARY STRESS INCONTINENCE

BACKGROUND OF THE INVENTION

The present invention relates to surgical treatment of female urinary stress incontinence.

In particular, the invention relates to a surgical assembly which, at the end of the procedure or operation, supports the urethra by a suburethral strip both of whose ends are disposed in an appropriate path of the body of the patient, for example to the abdominal wall thereof.

For this purpose, in general, the surgical assembly according to the present invention comprises a suburethral supporting strip and a needle or similar sharp part passed through the skin, said needle engaging and pulling the suburethral supporting strip.

SUMMARY OF THE INVENTION

The present invention relates to a surgical assembly as defined hereinabove, with a universal nature in the sense that it can be used whatever the surgical approach and technique selected by the practitioner.

For this purpose, a surgical assembly according to the invention has a combination of the following features:

a) it includes a composite band comprised of at least the suburethral supporting strip and a flat protective sheath, said strip being disposed for example freely inside this sheath;

b) the flat sheath includes, in its lengthwise direction, two parts disposed on either side of a central separation area;

c) at each of its two ends the composite band has a single part, for example a single female part, of a lockable and unlockable connecting means, while the percutaneous needle has at least one other part, for example a male part, of a connecting means, the connecting means of the composite band and each connecting means of the needle enabling the needle to be connected releasably to at least one of the ends of said composite band.

The needle may have connecting means at its proximal and distal ends.

The composite band may have a breakable linking means formed by an adhesive outer sleeve that can be torn off by a shearing force for example, connecting the two inside ends of the two parts of the flat sheath both of which are adjacent to the separating area.

For one of the approaches chosen by the surgeon, for example the high approach, the assembly additionally and possibly has a flat, flexible piece for joining two pieces of the supporting strip, obtained by cutting said strip transversely, said piece including two opposite means for gripping two adjacent ends of the two pieces, respectively.

The needle may be formed of a curved, sharp part of an instrument, able to pass through the bodily tissues of the patient, passing through the foramen of the pelvis until it emerges through the vaginal incision.

BRIEF DESCRIPTION OF FIGURES

The present invention will now be described with reference to the attached drawing wherein:

FIG. 1 is a front view of a surgical assembly according to the invention according to a first embodiment, FIG. 2 is a side view of the surgical assembly shown in FIG. 1, FIG. 3 is a cross-sectional view of a means for connecting with the percutaneous needle passing through the skin, belonging to the surgical assembly shown in FIGS. 1 and 2, FIG. 4 is a top view of a part joining two pieces of the supporting strip, which can belong to a surgical assembly according to the invention, FIG. 5 is a side view of the joining part shown in FIG. 7, with its two opposite gripping means in the open position, FIGS. 10 to 13 represent the various steps of placement or implementation of a surgical assembly according to the invention by a so-called "combined" approach, FIGS. 14 to 21 represent the various steps of placement or implementation of a surgical assembly according to the invention by a so-called "high" approach, FIG. 23 is a side view of a needle that can be used with this composite band, FIGS. 24 and 25 are views, respectively, of the side of the composite band and the face of the proximal part of the needle, FIGS. 30A and 30B are side views of an instrument usable with the composite band shown in FIGS. 22 and 24 for placement or implementation of a surgical assembly including this composite band and this instrument by a "transforaminal" approach.

DESCRIPTION OF EMBODIMENTS OF THE INVENTION

Figure 6:
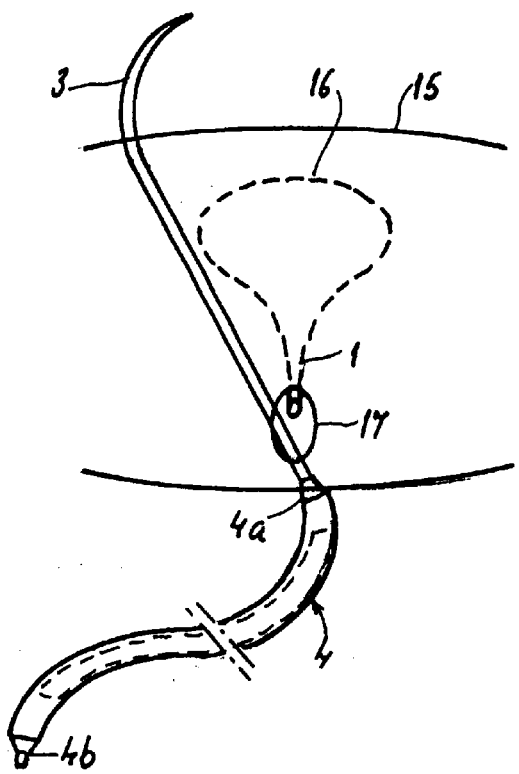
FIGS. 6 to 9 represent the various steps of placement or implementation of a surgical assembly according to the invention by a so-called "low" approach.

According to FIGS. 1 to 3, a surgical assembly according to the invention includes as a minimum:

a composite band 4 having two sharp ends 4a, 4b, which is triangular when flat, and a percutaneous needle 3 designed to pass through the skin having a penetrating distal end 32 and a flattened blunt proximal end 31.

Composite band 4 has, at least, a suburethral supporting strip 2, two end pieces 9, and a flat protective sheath 5 inside which strip 2 is freely disposed, i.e. unattached to sheath 5.

The supporting strip 2 includes a filet stitch fabric, preferably pinpoint, obtained with monofilaments or multifilaments of biocompatible synthetic material, for example polypropylene or polyester.

Strip 2 is preferable formed of a macroporous knit.

The latter is for example a polypropylene monofilament filet stitch fabric between 0.12 and 0.16 millimeter in width and composed of two layers formed by two bars, both threaded, with a full bar alternating with an empty bar, these two bars being moved symmetrically in open stitches according to the following scale:

bar I: 01-12-32 bar II: 32-21-01

Strip 2 is cut lengthwise in the direction of the knitting row. With a width of 12 mm, it has the following characteristics:

breaking strength in the direction of the knitting row of 105N±20%, elongation at rupture in the direction of the row of 92%±20%, elongation at 20N of 36%, initial curling with a force of 6N and elongation of 15%.

"Curling" is the spontaneous coiling of the strip 2 on itself, around its lengthwise axis when tensioned lengthwise.

Strip 2 has useful advantages, and in particular low particle emission when stretched, as well as curling which does not appear until a substantial force (6N). None of these features affects the porosity of strip 2.

The latter can also be made wholly or partially of biological tissue or material, for example collagen.

The flat, protective sheath 5 is obtained from a synthetic material with a low coefficient of friction, for example PTFE. This sheath 5 has in the lengthwise direction two parts 51 and 52 disposed on either side of a separation area 6 in which a breakable linking means 7 is disposed between said two parts.

Composite band 4 has, at each of its two ends 4a and 4b, a single part, namely a single female part 81, of a connecting means 8 that can be locked and unlocked as desired, while the blunt proximal end of percutaneous needle 3 has another part, for example a male part 82, of the same connecting means 8.

For this purpose, flat sheath 5 includes or incorporates, at its two ends respectively, two end pieces 9 that each include or incorporate, outside sheath 5, the same female part 81 of the connecting means 8.

This connecting means 8 thus has, according to the first embodiment, two elements, one male 82 located at each end 4a or 4b of composite band 4, and the other female 81, located at the blunt proximal end 31 of needle 3, these male and female elements being snappable into each other.

More specifically, as shown in particular in FIG. 3, the blunt proximal end 31 of percutaneous needle 3 is spatulate, and each end piece 9 of composite band 4 has, outside the flat sheath 5, a slot 83 designed for penetration of spatulate proximal end 31 of needle 3, with a manually lockable and unlockable means 84 for holding blunt end 31. Blunt proximal end 31 of needle 3 has a through-slot 85 for elastic penetration of the holding means 84.

According to FIG. 1, and according to a particular embodiment, the breakable linking means 7 consists of an outer sleeve 71, which is adhesive and can be torn off by a tab 72. This sleeve 71 has two inside ends 51a and 52a of the two parts 51 and 52 of flat sheath 5, which are respectively adjacent to separating area 6.

For the so-called high approach, described below, the surgical assembly also has a part 10 shown in FIGS. 4 and 5, designed to join the two pieces 21 and 22 of supporting strip 2 (see FIGS. 18 to 21), obtained by cutting the latter transversely.

This joining part 10, which is flat, flexible, atraumatic, has two opposite means that grip two adjacent ends 21a and 22a of two pieces 21 and 22, respectively. For this purpose, each gripping means 11 has both a means 12 for gripping one end 21 a or 22a (see FIGS. 18 to 21) of supporting strip 2, comprised of two flat jaws 12a and 12b articulated in one and the same joining line, and a means 13 for stapling the same end, consisting of a pin 13a on one jaw 12b to pass through strip 2 and a head 13b disposed on the other jaw 12a, snappable onto pin 13a.

Three different methods of placing or implementing the surgical assembly stated above will now be described, namely a low approach, a combined approach, and a high approach.

For each of these methods, the starting point is the surgical assembly according to FIGS. 1 to 3, in its connected or locked position, wherein needle 3 is connected by its blunt proximal end 31 with one of the end pieces 9, namely at one of the ends, for example 4a, of composite band 4, by means of the above-described connecting means 8.

Figure 7:
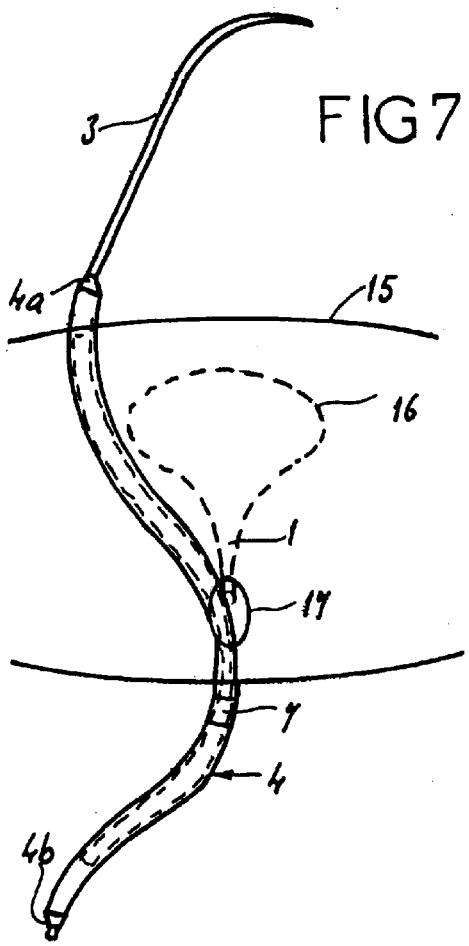
Figure 8:
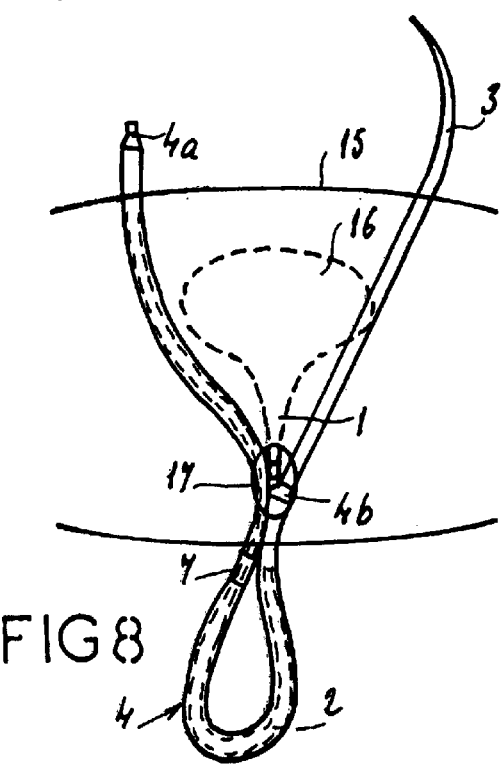
Figure 9:
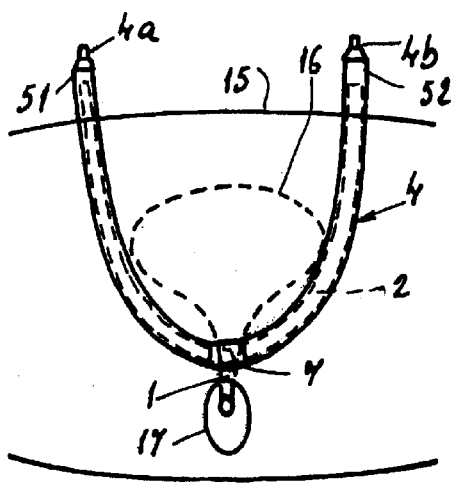

In the case of the low approach, with reference to FIGS. 6 to 9:

by inserting needle 3 through vagina 17, needle 3 is caused to penetrate upward, on the right side of the patient, in the retropubic space, avoiding bladder 16 (see FIG. 6);

hence, composite band 4 is engaged in the right path (see FIG. 7);

needle 3 is disconnected from end 4a of composite band 4 then connected to end 4b of the same strip; then needle 3 is inserted in the upward direction, on the left side of the patient, still in the retropubic space, avoiding bladder 16 (see FIG. 8);

thus, composite band 4 is engaged in the left path; when the latter forms a loop outside vagina 17, the linking means 7 is torn off transversely to release the two parts 51 and 52 of sheath 5; by pulling on the two end pieces 9, the two parts 51 and 52 of sheath 5 are extracted and supporting strip 2 is released below urethra 1.

In the case of the combined approach, with reference to FIGS. 10 to 13:

needle 3 is inserted downward, on the right side of the patient, in the retropubic space, avoiding bladder 16 and emerging through vagina 17 (see FIG. 10);

then, composite band 4 is engaged in the right path, then needle 3 is inserted upward, on the left side, in the retropubic space, avoiding bladder 16 (see FIG. 11);

thus, composite band 4 is engaged in the left path; needle 3 is disconnected from composite band 4; the linking means 7 is torn transversely by shearing outer sleeve 71 (see FIG. 12);

by pulling on the two end pieces 9, the two parts 51 and 52 of sheath 5 are extracted, and supporting strip 2 is released in its path (see FIG. 13).

Figure 18:
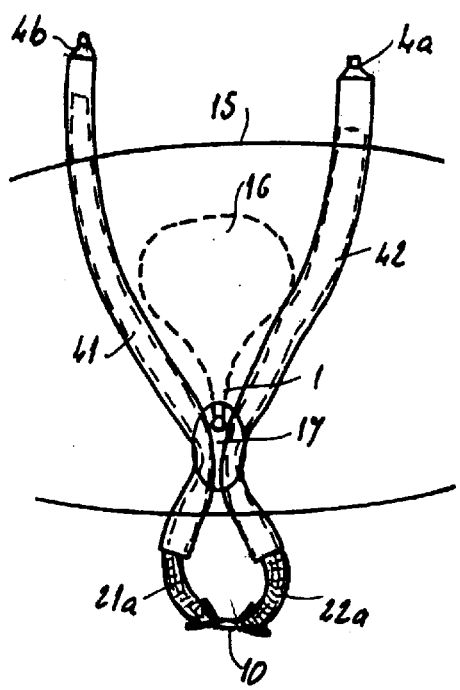
Figure 19:
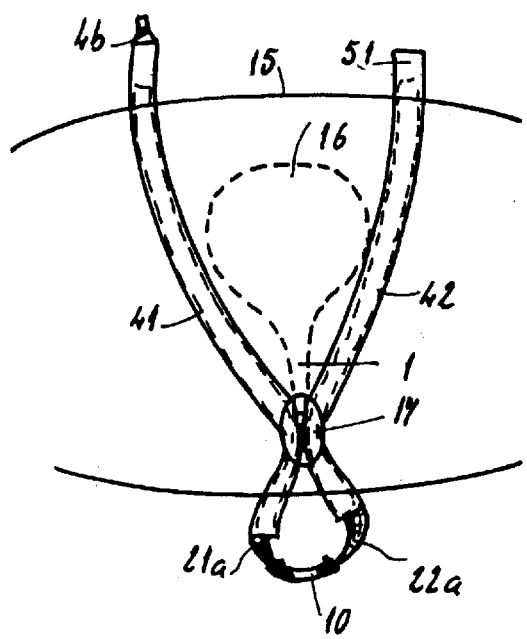
Figure 20:
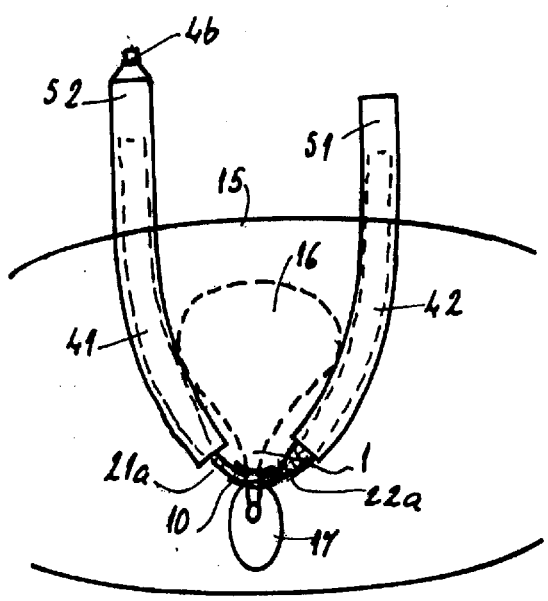
Figure 21:
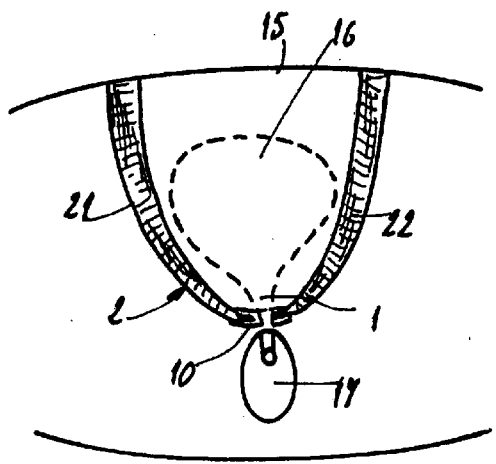

In the case of the high approach, with reference to FIGS. 14 to 21:

needle 3 is inserted downward, on the right side of the patient, from the abdominal wall 15, in the retropubic space, avoiding bladder 16 and emerging through vagina 17 (see FIG. 14);

thus, composite band 4 is engaged in the right path; when the linking means 7 is outside vagina 17, the composite band 4 is cut on either side of the vagina to form two parts, one part 41 remaining in the right path and one part 42 being outside the vagina 17 (see FIG. 15);

needle 3 connected to part 42 of composite band 4 is then inserted downward starting from the abdominal wall 15, on the left side, in the retropubic space, avoiding bladder 16 (see FIG. 16);

thus, part 42 of composite band 4 is engaged in the left path then the emerging portion of part 42 of composite band 4 is cut to separate corresponding end piece 9 from the rest of band 4 (see FIG. 17);

by pulling on ends 21a and 22a of supporting strip 2, these ends are stripped off the two parts 52 and 51 respectively of sheath 5; thus, the joining part 10 can be presented and the two ends 21 a and 22a can be gripped (see FIG. 18);

the joining part 10 thus securely joins the two ends 21a and 22a of supporting strip 2 outside vagina 17, as shown in FIG. 19;

then subpubic traction is applied to the right part 41 and left part 42 of composite band 4 in order to bring the joining part 10 into the suburethral position; then the two parts 52 and 51 of sheath 4 are pulled in order to release supporting strip 2 (see FIG. 20);

strip 2 is thus in the retropubic position, while the joining part 10, which is atraumatic, is in the suburethral position (see FIG. 21).

As stated above, it can be seen that a surgical assembly according to the invention can be used whatever the surgical approach and technique selected by the surgeon.

According to the invention, supporting strip 2 can be released at the last moment once the paths have been checked by cystoscopy.

If the path is incorrect on the first pass and/or on the second pass, the procedure can still be reversed, either by disconnecting needle 3 and pulling back on sheath 5, or by complete traction on composite band 4.

Provided sheath 5 has not been separated into its two parts 51 and 52, the surgical assembly according to the invention can be reused as often as necessary until the desired path has been achieved.

Figure 22:
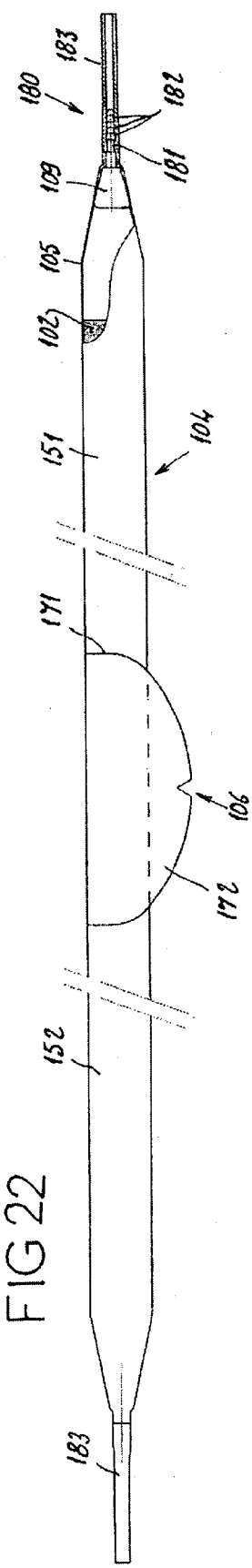
FIG. 22 is a front view of the composite band of a surgical assembly according to the invention according to a second embodiment.

Composite band 104 shown in FIGS. 22 and 24 is very similar to the band described above, having a strip 102, two end pieces 109, a sheath 105 in two parts 151, 152 inside which strip 102 is freely disposed, a separation area 106, a breakable outer sleeve 171 with a tab 172, and a means 180 for connecting the ends of composite band 104 to needle 103.

In this second embodiment of the invention, each means 180 for connecting band 104 has an axial finger 181 provided with circular projecting ribs 182 forming bulges, and an elastically deformable tubular portion 183 with a slightly smaller inside diameter than the diameter of finger 181.

Finger 181 is designed to make a friction connection in tubular portion 183, as ribs 182 cause circumferential stretching of the wall of this tubular portion 183, sufficient to create a strong link between finger 181 and tubular portion 183.

Figure 25:

As shown in FIGS. 23 and 25, a needle 103 usable with composite band 104 is also substantially similar to the needle 3 described above except that it has a proximal end 131 and a distal end 132 that are shaped for connection to tubular portion 183. For this to occur, each end 131, 132 has a conical end part 184 whose diameter increases in the direction of the central area of needle 103, and a cylindrical portion 185 whose diameter is smaller than the base diameter of conical portion 184, said cylindrical portion 185 also delimiting a shoulder with conical portion 184.

The base of conical portion 184 has a larger diameter than the inside diameter of tubular portion 183 and can make a friction connection with tubular portion 183, causing circumferential stretching of the wall of this tubular portion. This portion 184 also has a relatively steep slope and a small cross section so that it can penetrate the bodily tissues of the patient.

The portions 184 and 185 and tubular portion 183 thus enable a releasable connection of the tubular portion 183 to be created at either end 131, 132 of needle 103; this connection is sufficiently strong to withstand the pull produced by band 104 caused by the friction applied to this band 104 when it is engaged in the body of the patient, but is insufficiently strong to withstand the antagonist manual pulls applied to needle 103 and to the tubular portion 183 in order to separate this needle 103 from this tubular portion 183.

Portions 184 and 195 of the proximal end 131 of needle 103 are used to place the composite band 104 according to one of the approaches, "low," "combined," or "high," described above with reference to FIGS. 6 to 21; portions 184 and 185 of the distal end 132 of needle 103 are used to place composite band 104 according to a variant of the approach known as "high" shown in FIGS. 26 to 29.

Figure 26:
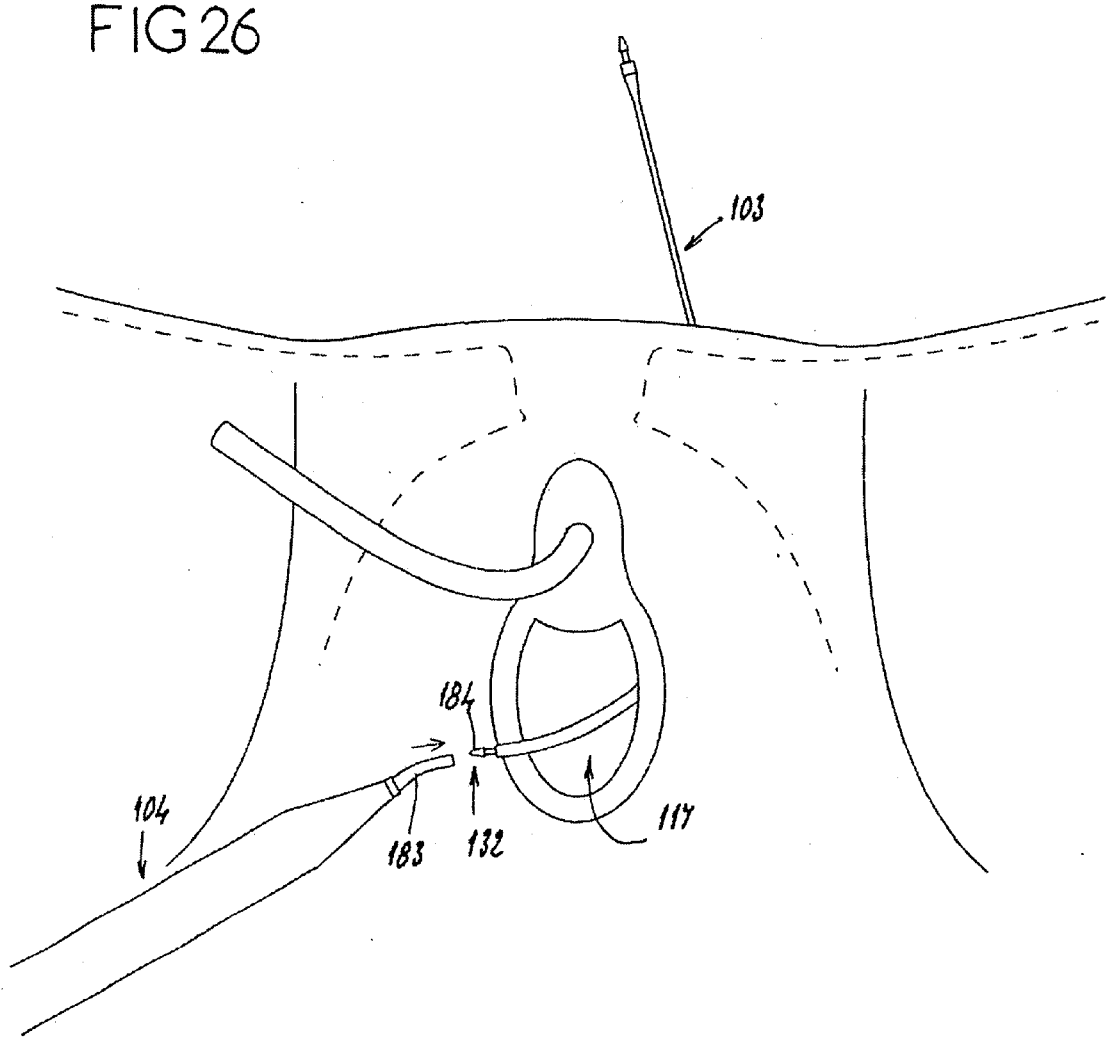
FIGS. 26 to 29 are views of four successive steps of placement or implementation of a surgical assembly according to the second embodiment by a so-called "high retropubic" approach.
Figure 27:
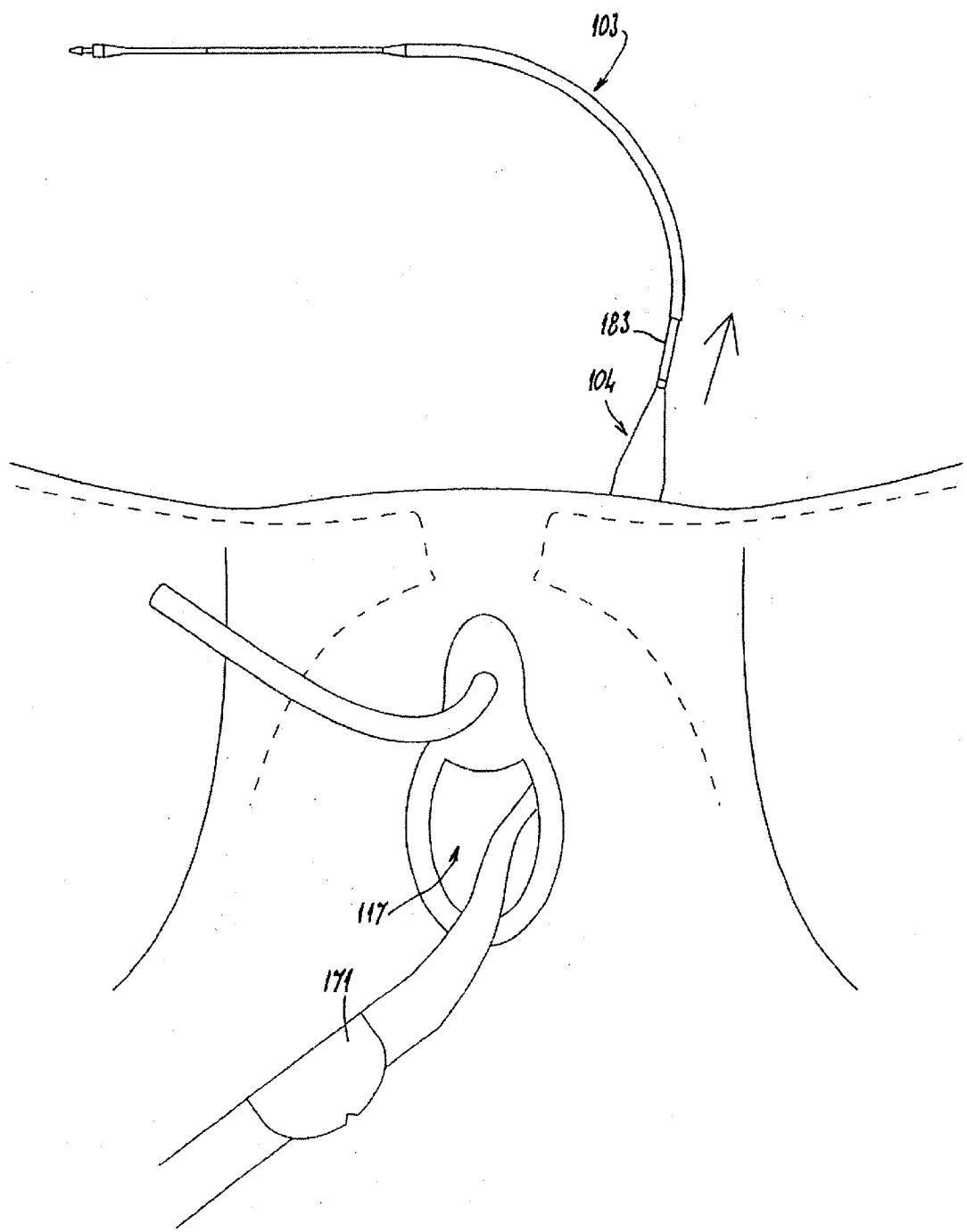
Figure 28:
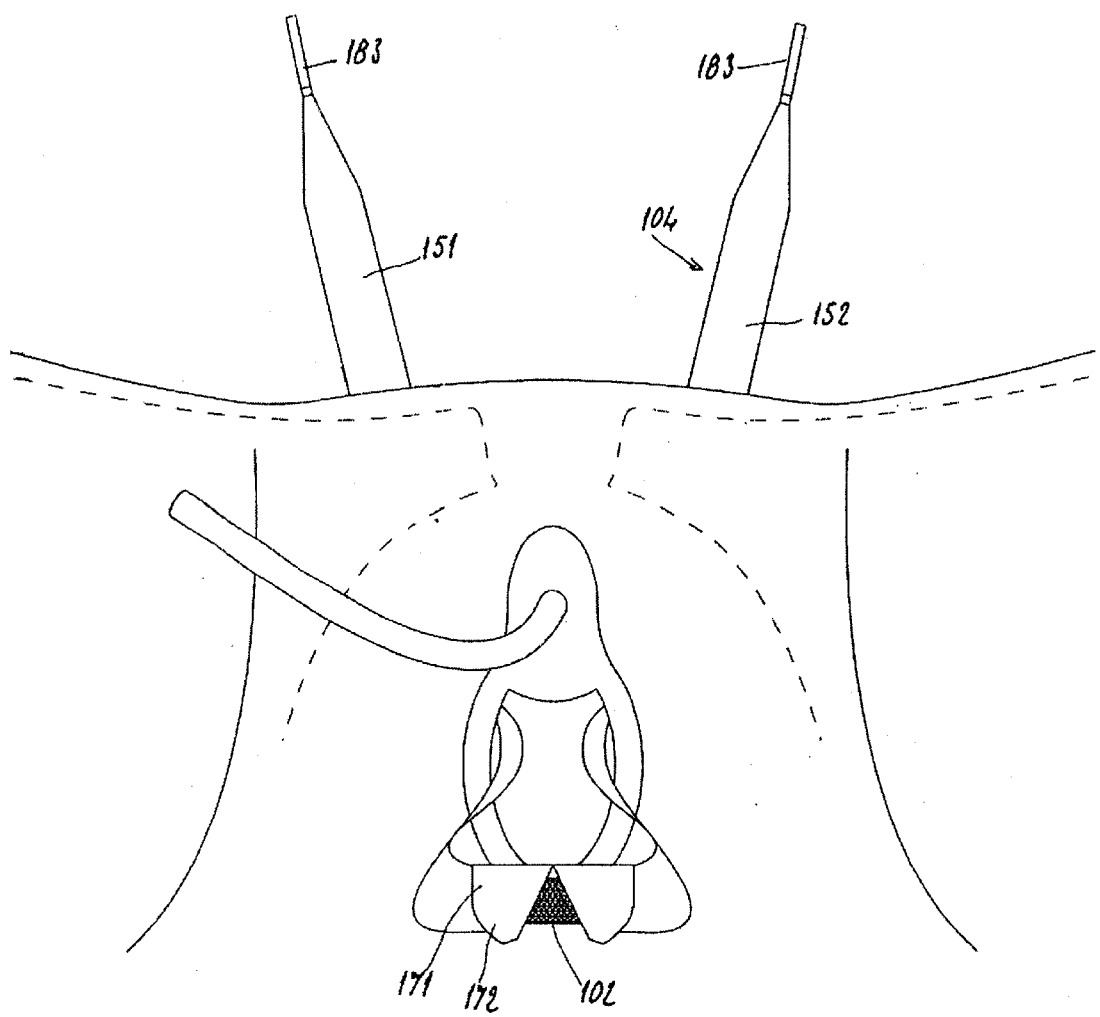

In the case of this "high retropubic" approach, needle 103 is inserted through the abdominal wall from a first subpubic incision up to a vaginal incision, then the distal end 132 emerging from vagina 117 is connected to the tubular portion 183 by one of the ends of band 104 (see FIG. 26). Needle 103 is then pulled back so that it engages composite band 104 through the path the needle 103 has created in the body of the patient until the end part of the half of band 104 connected to needle 103 at the subpubic level is made to emerge (see FIG. 27).

Figure 29:
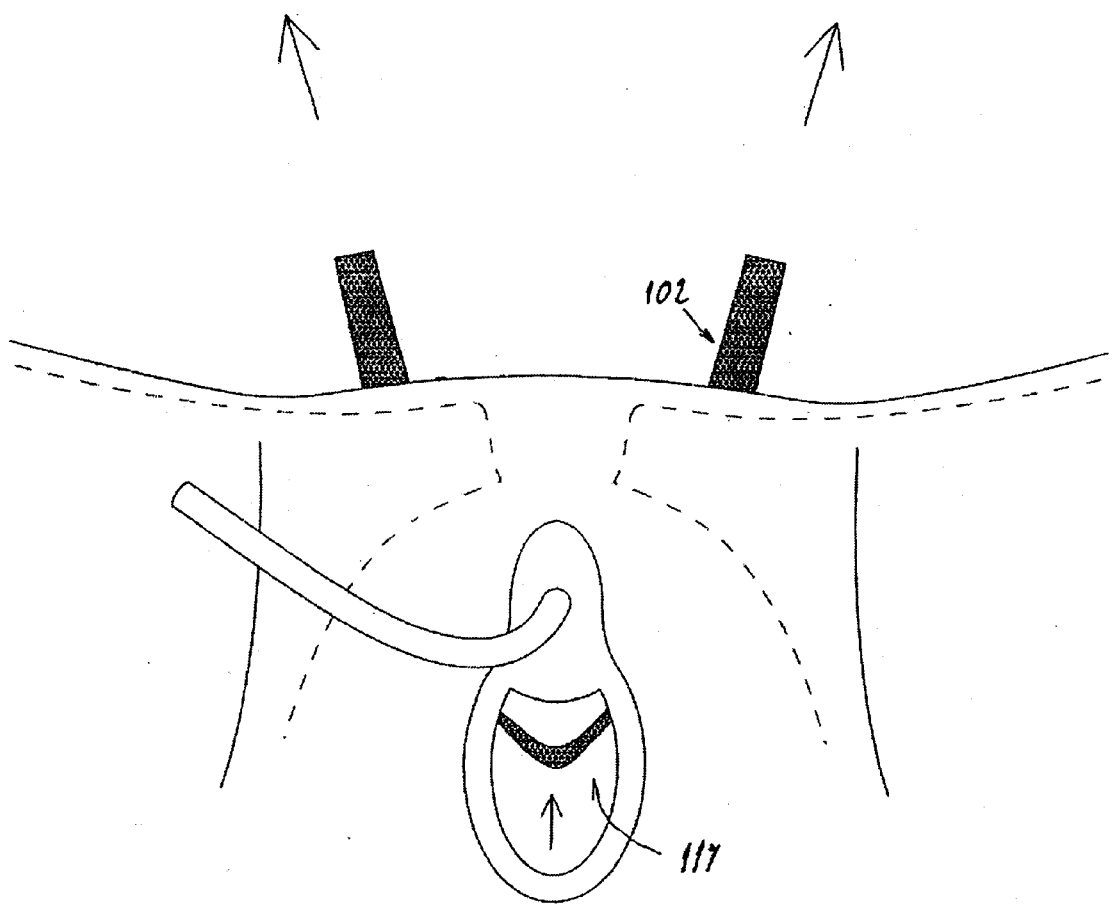

The same steps are taken on the other side since the sleeve 171 is broken by means of tab 172 (see FIG. 28), after which the sheath parts 151, 152 are removed from strip 102 and put in place (see FIG. 29).

Figure 31:
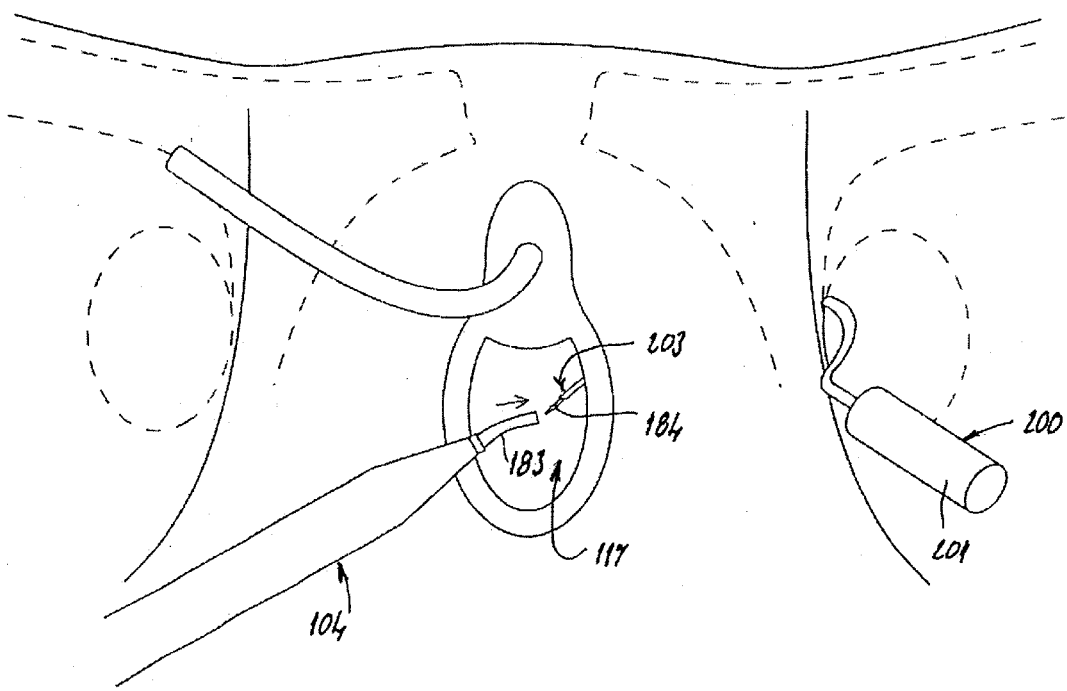
FIGS. 31 to 34 are views of four successive steps of placement or implementation of a surgical assembly comprising this composite band and this instrument by said "transforaminal" approach.

FIGS. 30A and 30B show an instrument 200 of which one part 201 forms a handle and the other sharp, curved part 203 forms a "needle" that can be inserted through the bodily tissues of the patient, passing through the foramen of the pelvis until it emerges through the vaginal incision, as shown in FIG. 31.

The sharp, curved part 203 has a rigid outer portion 205 integral with handle 201 and a flexible inner portion 206. This flexible inner portion 206 can slide along the radially internal face of the outer portion 205 and be actuated by a pushbutton 207 at its proximal end. Guide means are provided to slidably guide portion 206 along portion 205, particularly in the form of a groove provided in portion 205 in which a foot integral with portion 206 slides.

Portion 206 is movable relative to portion 205 between an advanced position shown in FIG. 30A and a retracted position shown in FIG. 30B; in the advanced position, the distal end of portion 206 forms, with the distal end of portion 205, a conical portion 284 with a steep slope and relatively small cross section enabling engagement of part 203 through the bodily tissues of the patient; in the retracted position, the distal end of portion 206 is retracted from the distal end of portion 205.

As shown in FIG. 30B, the distal end of portion 205 forms most of said conical portion 284 but has a proximal notch 285 delimiting a sharp edge. This distal end thus has a "harpoon" shape and is able to penetrate slightly into the wall of the tubular portion 183 when this tubular portion 183 is engaged thereon.

The distal end of portion 206 is shaped such that it occupies said proximal notch in the advanced position and completes the conical portion 284.

As shown in FIGS. 31 to 34, part 203 is engaged through the bodily tissues of the patient, passing through the foramen of the pelvis until it emerges from vagina 117, when portion 206 is the in the advanced position. Pushbutton 207 is then actuated in order to retract portion 206 then the tubular portion 183 of one end of band 104 is engaged on the distal harpoon-shaped end of portion 205; this engagement enables penetration of this distal end into the wall of tubular portion 183 and thus enables a link to be formed between this tubular portion 183 and the distal end of portion 205 (see FIG. 31).

Figure 32:
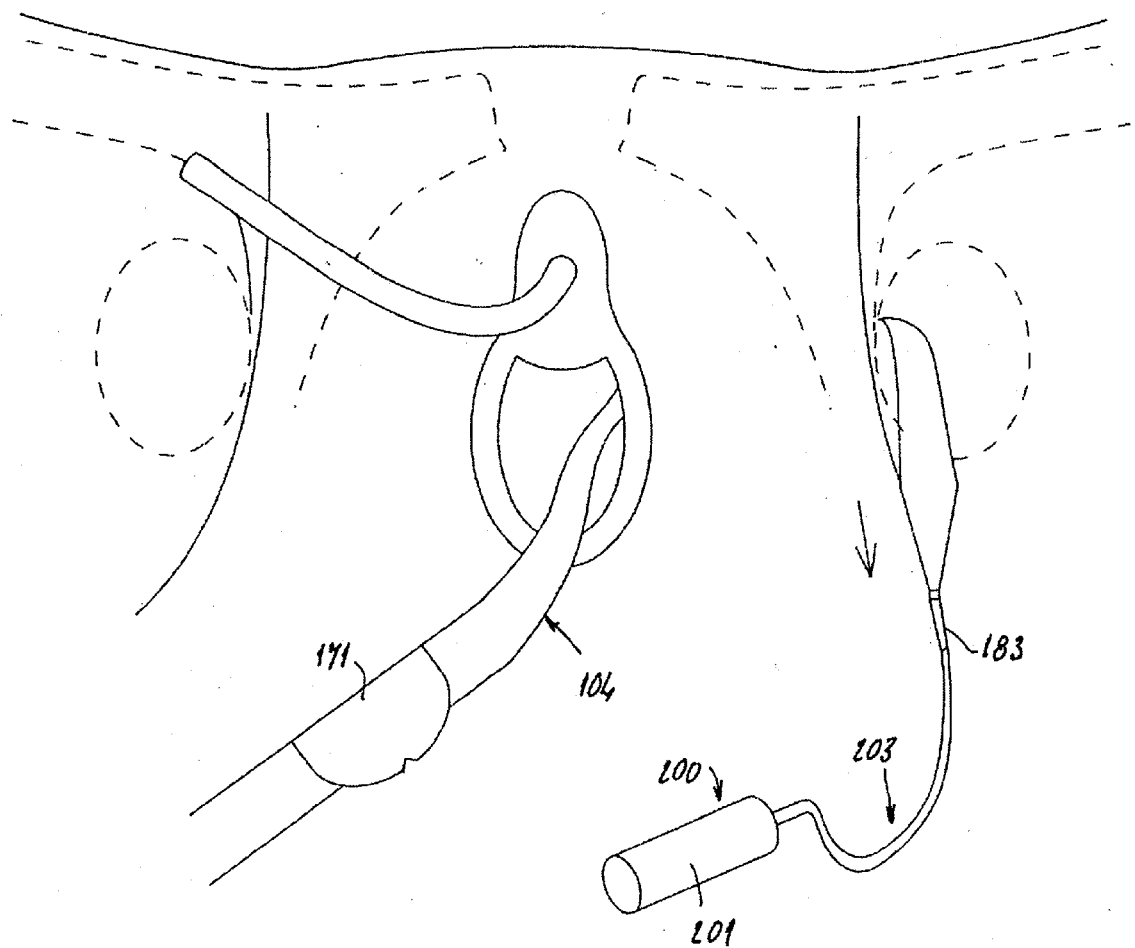
Figure 33:
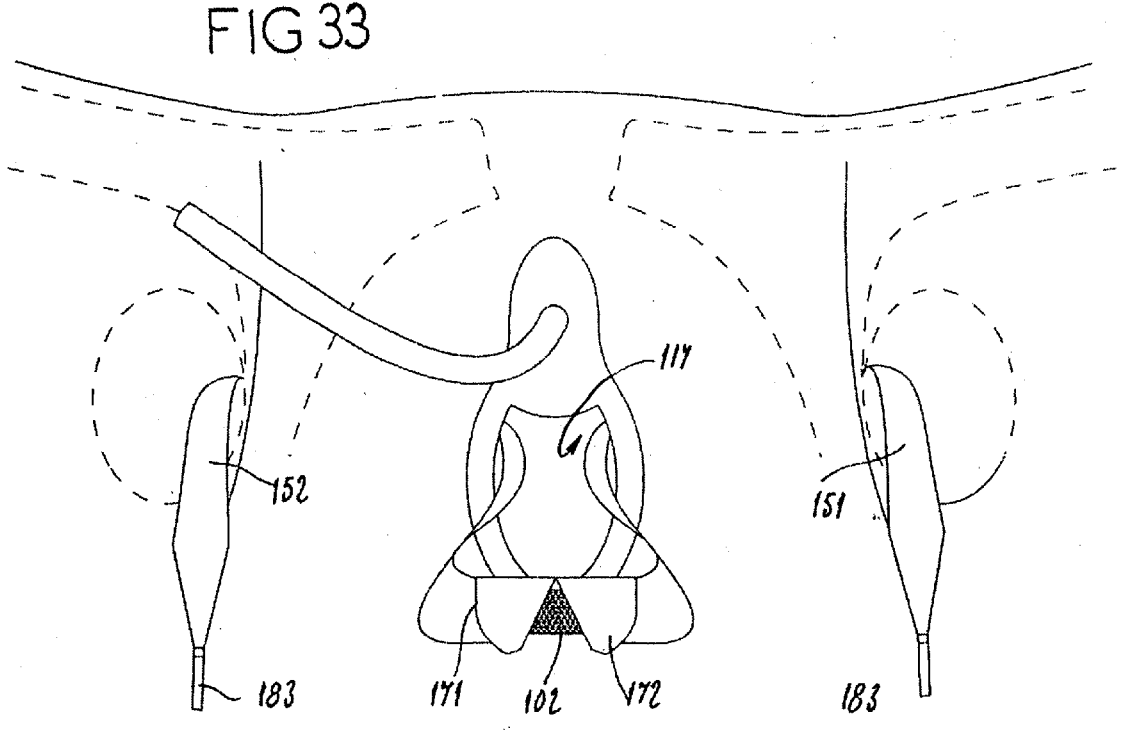
Figure 34:
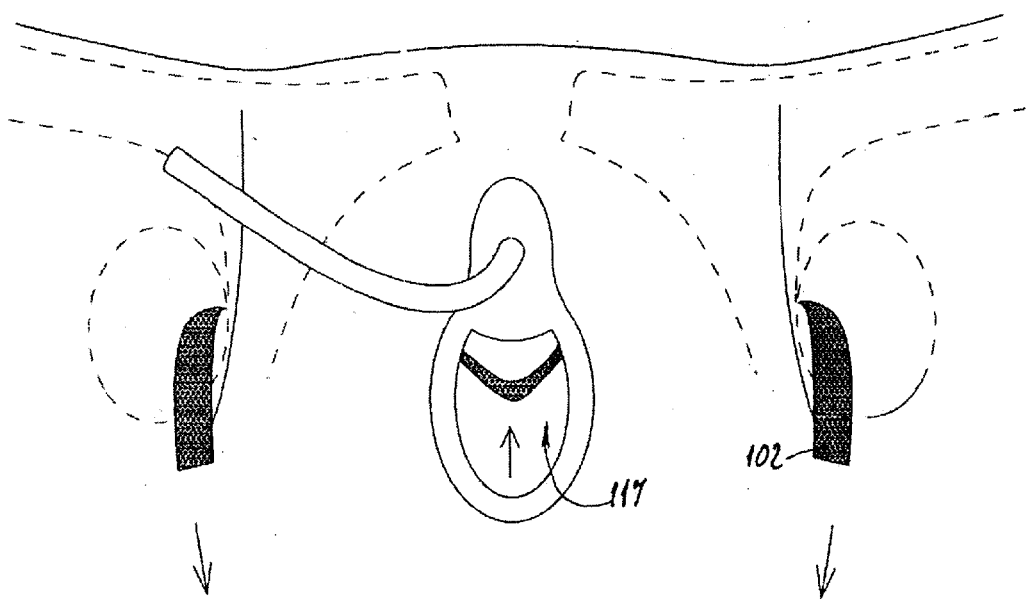

Instrument 200 is then drawn back so as to engage half the band 104 connected to part 203 through the path in the body created by means of this instrument (see FIG. 32).

The end 184 of the needle is disconnected from tube 183 and the same operations are performed on the other side. The two sheath parts 151, 152 are then separated and withdrawn (see FIG. 33) and strip 102 is set in place by pulling on its emerging ends (see FIG. 34).

What is claimed is:

1. Surgical assembly for supporting the urethra of a female patient, comprising a composite band, a suburethral supporting strip and a percutaneous needle or similar sharp part designed to pass through the skin of the patient, wherein:
   a) the composite band comprises at least the suburethral supporting strip and a flat protective sheath;
   b) the flat sheath includes, in its lengthwise direction, two parts disposed on either side of a central separation area;
   c) each of two ends of the flat sheath of the composite band has a single part of a lockable and unlockable connecting means, and the percutaneous needle has at least one other part of a connecting means, the connecting means of the composite band and each connecting means of the needle enabling the needle to be connected releasably to at least one of the ends of said composite band.

2. Assembly according to claim 1, wherein the needle has connecting means at its proximal and distal ends.

3. Assembly according to claim 1, wherein the composite band has two end pieces each including or incorporating the same part of the connecting means.

4. Assembly according to claim 1, wherein the connecting means has two elements, one male and the other female, snappable into each other.

5. Assembly according to claim 4, wherein the proximal end of the percutaneous needle is blunt and spatulate and each end piece of the flat sheath has a slot, designed for penetration of said spatulate proximal end, with a holding means for holding said spatulate proximal end that is manually lockable and unlockable.

6. Assembly according to claim 5, wherein the blunt proximal end of the percutaneous needle has a through-slot for penetration of the holding means.

7. Assembly according to claim 1, wherein the central separation area of the composite band has a breakable linking means formed by an adhesive outer sleeve that can be torn off, connecting two inside ends of the two parts of the flat sheath, both of which are adjacent to the central separating area.

8. Assembly according to claim 1, wherein said assembly additionally includes a flat, flexible piece for joining two pieces of the supporting strip obtained by cutting said strip transversely, said flexible piece including two opposite gripping means for gripping two adjacent ends of the two pieces, respectively.

9. Assembly according to claim 8, wherein each gripping means includes a means for gripping one end of the supporting strip.

10. Assembly according to claim 8, wherein each gripping means includes a means for stapling one end of the supporting strip.

11. Assembly according to claim 10, wherein said means for stapling one end of the supporting strip comprises a pin to pass through the strip with a head snappable onto said pin.

12. Assembly according to claim 1, wherein the supporting strip includes a filet stitch fabric, made of monofilaments or multifilaments of a biocompatible synthetic material.

13. Assembly according to claim 12, wherein said biocompatible synthetic material is at least one member selected from the group consisting of polypropylene and polyester.

14. Assembly according to claim 12, wherein said assembly additionally includes a flat, flexible piece for joining two pieces of the supporting strip obtained by cutting said strip transversely, said flexible piece including two opposite gripping means for gripping two adjacent ends of the two pieces, respectively.

15. Assembly according to claim 1, wherein the supporting strip is fully or partially made of biological tissue or material.

16. Assembly according to claim 15, wherein said biological tissue or material is collagen.

17. Assembly according to claim 15, wherein said assembly additionally includes a flat, flexible piece for joining two pieces of the supporting strip obtained by cutting said strip transversely, said flexible piece including two opposite gripping means for gripping two adjacent ends of the two pieces, respectively.

18. Assembly according to claim 1, wherein the protective sheath is obtained from a synthetic material with a low coefficient of friction.

19. Assembly according to claim 18, wherein said synthetic material is PTFE.

20. Assembly according to claim 18, wherein said assembly additionally includes a flat, flexible piece for joining two pieces of the supporting strip obtained by cutting said strip transversely said flexible piece including two opposite gripping means for gripping two adjacent ends of the two pieces, respectively.

21. Assembly according to claim 1, wherein each connecting means has an axial finger provided with projecting circular ribs, forming bulges, and an elastically deformable tubular portion whose inside diameter is slightly less than the diameter of the finger.

22. Assembly according to claim 21, wherein at least the proximal end of the needle has a conical terminal part whose diameter increases towards a central area of the needle, and a cylindrical portion with a smaller diameter than a base diameter of the conical portion, said cylindrical portion thus delimiting a shoulder with the base of the conical portion, said base of said conical portion having a larger diameter than the inside diameter of the tubular portion and being frictionally engageable in said tubular portion, causing circumferential stretching of a wall of the tubular portion, said conical portion also having a steep slope and a small cross section such that said conical portion is able to pierce the bodily tissues of the patient.

23. Assembly according to claim 21, wherein the needle is formed of a curved, sharp part of an instrument, able to pass through bodily tissues of the patient by passing through the foramen of the pelvis of the patient until it emerges through a vaginal incision.

24. Assembly according to claim 23, wherein said curved, sharp part has a rigid outer portion and a flexible inner portion that can slide along a radially inner face of said rigid outer portion, said rigid outer portion and said flexible inner portion having distal ends; said flexible inner portion being movable relative to said rigid outer portion between an advanced position and a retracted position;

wherein in said advanced position, the distal end of said flexible inner portion forms, with the distal end of said rigid outer portion, a conical portion with a steep slope and relatively small cross section enabling engagement of said curved, sharp part through bodily tissues of the patient; and wherein in said retracted position, the distal end of the flexible inner portion is retracted from the distal end of the rigid outer portion; the distal end of the rigid outer portion having a proximal notch delimiting a sharp edge giving it a harpoon shape and, in this retracted position, is able to penetrate into the wall of said tubular portion when this tubular portion is engaged therewith.

25. Assembly according to claim 21, wherein said assembly additionally includes a flat, flexible piece for joining two pieces of the supporting strip obtained by cutting said strip transversely, said flexible piece including two opposite gripping means for gripping two adjacent ends of the two pieces, respectively.

26. Assembly according to claim 1, wherein said strip is disposed freely inside said flat sheath.

27. Method for placement or implementation of a surgical assembly according to claim 1, comprising:

connecting the needle to a first end of the composite band;

inserting the needle and first end through the vagina of the patient, whereby the needle is caused to penetrate upward, on one side of the patient, bypassing the bladder of the patient, and the composite band is engaged in a path in the body thus created;

disconnecting the needle from the first end of the composite band and connecting the needle to the second end of the composite band;

inserting the needle and second end in an upward direction, on the other side of the patient, bypassing the bladder, whereby the composite band is engaged in the bodily path thus created;

disconnecting the needle from the second end of the composite band; and extracting the two parts of the sheath, thus releasing the supporting strip below the urethra.

28. Method for placement or implementation of a surgical assembly according to claim 1, comprising:

inserting the needle downward, on one side of the patient, bypassing the bladder of the patient and emerging through the vagina of the patient;

inserting the needle upward, on the other side of the patient, bypassing the bladder and emerging at a subpubic level;

disconnecting the needle from the composite band; and extracting the two parts of the sheath, thus releasing the supporting strip below the urethra.

29. Method for placement or implementation of a surgical assembly according to claim 8, comprising:

inserting the needle downward, on a first side of the patient, through the abdominal wall of the patient, bypassing the bladder of the patient and emerging through the vagina of the patient, thus engaging the composite band in the bodily path thus created when the connecting means is outside the vagina;

cutting one side of said composite band to create two parts, one part remaining inside said path and the other part outside the vagina;

inserting the needle connected to the other part of the composite band downward from the second side of the abdominal wall, bypassing the bladder and emerging through the vagina, thus engaging said other part of the composite band in the bodily path so created;

cutting the emerging portion of said other part of the composite band;

pulling on the two parts of the sheath, thus stripping the two parts of the composite band and putting said flexible piece in place;

applying subpubic traction to the two parts of the composite band in order to bring the flexible piece to a suburethral position; and withdrawing the two parts of the sheath to release the supporting strip.

30. Method for placement or implementation of a surgical assembly according to claim 14, comprising:

a) inserting the needle through the abdominal wall of the patient from a subpubic incision until it emerges from the vagina of the patient;

b) connecting the distal end of the needle emerging from the vagina to said tubular portion of one of the two ends of the composite band;

c) retracting the needle so as to engage the composite band through the bodily path that the needle has created until the composite band emerges at a subpubic level;

d) repeating steps a)–c) on the other side of the pelvis of the patient; and e) withdrawing the two sheath parts thus putting the strip in place.

31. Method for placement or implementation of a surgical assembly according to claim 17, comprising:

a) inserting said curved, sharp part through the bodily tissues through the foramen of the pelvis until the curved, sharp part emerges from the vagina of the patient, said flexible inner portion being in the advanced position, b) retracting said flexible inner portion;

c) engaging the tubular portion of one end of the composite band with the harpoon-shaped distal end of said rigid outer portion;

d) withdrawing said curved, sharp part in order to engage the composite band through the bodily path created by the curved, sharp part;

e) repeating steps a)–d) on the other side of the pelvis;

f) withdrawing the two sheath parts; and g) setting the strip in place by pulling on the strip's emerging ends.

32. Method for placement or implementation of a surgical assembly according to claim 14, comprising:

inserting the needle downward, on a first side of the patient, through the abdominal wall of the patient, bypassing the bladder of the patient and emerging through the vagina of the patient, thus engaging the composite band in the bodily path thus created when the connecting means is outside the vagina;

cutting one side of said composite band to create two parts, one part remaining inside said path and the other outside the vagina;

inserting the needle connected to the other part of the composite band downward from a second side of the abdominal wall, bypassing the bladder and emerging through the vagina, thus engaging said other part of the composite band in the bodily path so created;

cutting the emerging portion of said other part of the composite band;

pulling on the two parts of the sheath, thus stripping the two parts of the composite band and putting said flexible piece in place;

applying subpubic traction to the two parts of the composite band in order to bring the flexible piece to a suburethral position; and withdrawing the two parts of the sheath to release the supporting strip.

33. Method for placement or implementation of a surgical assembly according to claim 17 comprising:

inserting the needle downward, on a first side of the patient, through the abdominal wall of the patient, bypassing the bladder of the patient and emerging through the vagina of the patient, thus engaging the composite band in the bodily path thus created when the connecting means is outside the vagina;

cutting one side of said composite band to create two parts, one part remaining inside said path and the other outside the vagina;

inserting the needle connected to the other part of the composite band downward from second side of the abdominal wall, bypassing the bladder and emerging through the vagina, thus engaging said other part of the composite band in the bodily path so created;

cutting the emerging portion of said other part of the composite band;

pulling on the two parts of the sheath, thus stripping the two parts of the composite band and putting said flexible piece in place;

applying subpubic traction to the two parts of the composite band in order to bring the flexible piece to a suburethral position; and withdrawing the two parts of the sheath to release the supporting strip.

34. Method for placement or implementation of a surgical assembly according to claim 20, comprising:

inserting the needle downward, on a first side of the patient, through the abdominal wall of the patient, bypassing the bladder of the patient and emerging through the vagina of the patient, thus engaging the composite band in the bodily path thus created when the connecting means is outside the vagina;

cutting one side of said composite band to create two parts, one part remaining inside said path and the other outside the vagina;

inserting the needle connected to the other part of the composite band downward from a second side of the abdominal wall, bypassing the bladder and emerging through the vagina, thus engaging said other part of the composite band in the bodily path so created;

cutting the emerging portion of said other part of the composite band;

pulling on the two parts of the sheath, thus stripping the two parts of the composite band and putting said flexible piece in place;

applying subpubic traction to the two parts of the composite band in order to bring the flexible piece to a suburethral position; and withdrawing the two parts of the sheath to release the supporting strip.

35. Method for placement or implementation of a surgical assembly according to claim 25, comprising:

inserting the needle downward, on a first side of the patient, through the abdominal wall of the patient, bypassing the bladder of the patient and emerging through the vagina of the patient, thus engaging the composite band in the bodily path thus created when the connecting means is outside the vagina;

cutting one side of said composite band to create two parts, one part remaining inside said path and the other outside the vagina;

inserting the needle connected to the other part of the composite band downward from a second side of the abdominal wall, bypassing the bladder and emerging through the vagina, thus engaging said other part of the composite band in the bodily path so created;

cutting the emerging portion of said other part of the composite band;

pulling on the two parts of the sheath, thus stripping the two parts of the composite band and putting said flexible piece in place;

applying subpubic traction to the two parts of the composite band in order to bring the flexible piece to a suburethral position; and withdrawing the two parts of the sheath to release the supporting strip.

\* \* \* \* \*

UNITED STATES PATENT AND TRADEMARK OFFICE
CERTIFICATE OF CORRECTION

PATENT NO. : 6,685,629 B2
DATED : February 3, 2004
INVENTOR(S) : Michel Therin

It is certified that error appears in the above-identified patent and that said Letters Patent is hereby corrected as shown below:

<u>Column 10,</u>
Line 12, "assembly according to claim 14, comprising:" should read -- assembly according to claim 21, comprising: --
Line 27, "assembly according to claim 17, comprising:" should read -- assembly according to claim 24, comprising: --

Signed and Sealed this

Twenty-eighth Day of December, 2004

JON W. DUDAS
*Director of the United States Patent and Trademark Office*